(12) United States Patent
Schulz-Walz (10) Patent No.: US 8,702,425 B2
(45) Date of Patent: Apr. 22, 2014

(54) ELASTIC TEMPORARY SUPRACONSTRUCTION FOR A DENTAL IMPLANT

(75) Inventor: Jan Erik Schulz-Walz, Hamburg (DE)

(73) Assignee: VOCO GmbH, Cuxhaven (DE)

( * ) Notice: Subject to any disclaimer, the term of this patent is extended or adjusted under 35 U.S.C. 154(b) by 752 days.

(21) Appl. No.: 12/442,963

(22) PCT Filed: Sep. 26, 2007

(86) PCT No.: PCT/EP2007/060236
§ 371 (c)(1),
(2), (4) Date: May 13, 2009

(87) PCT Pub. No.: WO2008/037753
PCT Pub. Date: Apr. 3, 2008

(65) Prior Publication Data
US 2010/0086897 A1  Apr. 8, 2010

(30) Foreign Application Priority Data

Sep. 26, 2006 (DE) .......................... 10 2006 045 466

(51) Int. Cl.
*A61C 5/08* (2006.01)
*A61C 8/00* (2006.01)

(52) U.S. Cl.
USPC ..................... 433/218; 433/201.1; 433/202.1; 433/172; 264/19

(58) Field of Classification Search
USPC ........... 433/201.1, 202.1, 205, 206, 218–223, 433/49, 167–183; 264/16–20; 428/542.8; 29/896.11; 106/35; 523/116–120
See application file for complete search history.

(56) References Cited

U.S. PATENT DOCUMENTS

| | | | |
|---|---|---|---|
| 4,687,443 A * | 8/1987 | Driskell | 433/173 |
| 4,731,020 A | 3/1988 | Kawahara et al. | |
| 4,738,622 A | 4/1988 | Kawahara et al. | |
| 4,957,437 A | 9/1990 | Shimura et al. | |
| 5,885,077 A | 3/1999 | Jeffer | |
| 6,019,604 A | 2/2000 | Gougeon | |
| 6,283,753 B1 * | 9/2001 | Willoughby | 433/172 |
| 6,561,807 B2 * | 5/2003 | Hare | 433/214 |
| 6,805,556 B2 * | 10/2004 | Kiyomi | 433/168.1 |
| 2003/0003128 A1 | 1/2003 | Chiarelli | |
| 2003/0003423 A1 * | 1/2003 | Kangasniemi et al. | 433/222.1 |
| 2008/0241789 A1 | 10/2008 | Mundorf | |

FOREIGN PATENT DOCUMENTS

| | | |
|---|---|---|
| DE | 3904237 | 8/1989 |
| DE | 4326841 | 2/1995 |
| WO | WO 2005/018479 | 3/2005 |
| WO | WO 2006/033098 | 3/2006 |

OTHER PUBLICATIONS

"Silicones," Apr. 15, 2003, Encyclopedia of Polymer Science and Technology, John Wiey & Sons, Inc., US, pp. 765-841, XP007918236.

* cited by examiner

*Primary Examiner* — Yogesh Patel
(74) *Attorney, Agent, or Firm* — Duane Morris LLP; J. Rodman Steele, Jr.; Gregory M. Lefkowitz (57) ABSTRACT

A temporary supraconstruction for a dental implant or a core for a temporary supraconstruction for a dental implant, characterized in that it includes a material having a modulus of elasticity of less than 300 MPa, preferably in the range of from 15 to 20 MPa.

16 Claims, 2 Drawing Sheets

ELASTIC TEMPORARY SUPRACONSTRUCTION FOR A DENTAL IMPLANT

CROSS REFERENCE TO RELATED APPLICATIONS

This application is the entry into the United States of PCT Application No. PCT/EP2007/060236, filed Sep. 26, 2007 and claims priority from German Application No. 10 2006 045 466.9, filed Sep. 26, 2006, the entirety of each of which are hereby incorporated by reference.

BACKGROUND OF THE INVENTION

The present invention relates to a temporary supraconstruction for a dental implant comprising a material having a modulus of elasticity of less than 300 MPa, to the use of a material of this type for producing a temporary supraconstruction, to a kit and to a method for producing a temporary supraconstruction and also to an abutment for fastening a temporary supraconstruction.

In modern dentistry, the use of dental implants is a complex, but otherwise reliable and also aesthetically appealing treatment method for attending to tooth gaps.

Implants have significant advantages over the alternative possibilities of dental prosthesis such as fixed, non-implant-supported bridges or removable prostheses; in particular, they load the jaw bone in almost the same way as the original tooth. A dental implant is an artificial tooth root usually in the technical configuration of a screw which is implanted into the jaw bone when the tooth has become lost along with its root. As a result of the fact that the implant grows together with the bone, the implant assumes almost the same functions as the original tooth root and likewise introduces forces into the bone, thus subjecting the bone to tensile stress. As a result of this loading of the jaw bone, the bone metabolism is actively stimulated and supported, so that the jaw bone is preserved, whereas over time it recedes under bridges or with prostheses. The toothless jawbone, covered only by the gum, under total prostheses, on the other hand, is, as a result of the lack of the introduction of tensile force into the bone and additionally surface-active pressure, misloaded and decomposes more and more over the years, at times slowly, at times rapidly. As bone decomposition advances, it changes the entire bone bearing, and over the years this leads to major problems.

Dental implants are therefore inserted into the jaw bone in order, after taking thereof, to allow, compared to attendance without implants, better prosthetic attendance for the patient and to maintain the bone in situ. Thus, as a result, total prostheses are often avoided in toothless patients, as the patient can be attended to with either a denture secured to the implant or a combined secured/removable denture. In sets of teeth with gaps, the grinding of healthy teeth for the production of conventional (non-implant-supported) bridges can be avoided.

SUMMARY OF THE INVENTION

Implantological intervention is highly extensive and includes substantially the following steps:
  inserting the implant into the jaw bone
  taking of the implant into the bone
  exposing the implant
  taking an imprint using special imprint aids
  producing the denture (the supraconstruction)
  try-in of the denture manufactured by dentistry
  inserting the final denture (final attendance to the implant)

The term "supraconstruction" refers in the context of the present text to an element which is to be connected or is connected directly or indirectly to a dental implant and is provided to protrude completely or almost completely into the oral cavity. Generally, the supraconstruction is a denture. A supraconstruction can be for example a crown, a bridge (or a part of a bridge) or a removable prosthesis (or a part of a removable prosthesis). The term "final", such as for example in the context "final supraconstruction" or "final denture", denotes in the context of the present text an element which is not intended from the outset to be replaced by another element after a certain period of time. In contrast thereto, the term "temporary appliance" refers in the context of the present text to an element which is intended from the outset to be replaced by another element at a later point in time. The adjective "temporary" is to be understood accordingly. Generally, a connecting element, known as an abutment (construction), is provided between the implant and supraconstruction. An optionally present abutment is in the context of the present text not included in the supraconstruction. The term "connecting" of a temporary supraconstruction to a dental implant refers to both a positioning of the supraconstruction directly on the implant (without the use of an abutment) and a positioning of the supraconstruction on an abutment which is positioned on the implant (indirect connecting).

In the above-specified treatment sequence, the taking phase lasts generally between 2 and 6 months. This involves what is known as osseointegration of the implant. This means that bone grows onto the implant surface and the implant is securely anchored in the bone. However, this does not yet lead to an optimum architectonic orientation of the bone structure which can accommodate or at least optimally accommodate and optimally transmit forces. The above-specified treatment sequence causes, during the subsequent exposure of the implant and as a result of the subsequent attending to the implants with the prosthetic work (the supraconstruction), an abrupt, one hundred-percent transmission of forces, i.e. a complete transmission, which starts without a transition phase, of the forces generated during chewing, onto the implant which was previously unloaded by forces and the unloaded surrounding bone structure. The drawback of the above-specified treatment sequence is therefore the immediately occurring, one hundred-percent loading of the implants and surrounding bone structure, which may not correspond to the bone situation around the implant and overloads the bone in certain situations.

In order to attain good osseointegration, the bone and the cells present therein require time to grow onto the surface of the implant and to reconstruct surrounding bone. In the past, it was assumed that time and the quality of the bone are responsible for the taking speed and also for the success of the osseointegration. It has been discussed whether physiological forces acting on the implant promote osseointegration. It has been argued that physiological forces would load the bone structure which is produced only in so far as the taking process which has occurred to that point allows. It is believed that such an introduction of physiological force and an improvement resulting therefrom in the taking process allows the taking time to be shortened.

How long the taking time should be without the application of such a process of the introduction of physiological force is determined by acknowledged classifications of the density and structure of the bone, which define recommendations for specific taking times. Generally, these are 6 months for the upper jaw and 3 months for the lower jaw, as different bone structures and qualities may be found here.

A further important precondition for successful implantation is the fact that the implant has, once introduced into the bone, what is known as primary stability. That means that immediately after introduction it may not sit loose, but rather is anchored absolutely, i.e. to the maximum extent possible, securely in the bone; this can also be measured with the aid of apparatuses such as those sold under the name Periotest®. Interestingly, after the initial primary stability, the implant often becomes after about 14 days somewhat looser, in order then to become tighter again. This is explained by bone decomposition and reconstruction processes. Within this time, it is likely that the implant will be very sensitive to external force influences.

Recent years have seen a rethinking of the taking times required after the insertion of an implant. Heeding above all the desire of patients no longer to have to wait so long until the final attendance, practitioners have started to operate with shortened taking times or without taking times altogether and in accordance with the aforementioned alternative with immediate (immediately after the implantation or within 24 to 36 hours thereafter) temporary or final attendance to the implant and loading.

Studies on the immediate loading of implants compared to the conventional method are contradictory. There are studies which showed that the taking attained was less good in immediate implantation (M. Lorenzoni, C. Pertl, K. Zhang, W. Wegschneider, Clin. Oral Implants Res., 2003, 14 (3) 273-279); other studies found no difference (P. Quinlan et al., Int. J. Oral Maxillofac Implants 2005, 20 (3), 360-370) or reached the reservation that the patients are to be selected precisely and the load forces acting on the implants to be kept as low as possible (G. Romanos, J. Oral Implantol. 2004, 30 (3), 189-197).

The failures in immediate loading would appear to be due to premature and excessive transmissions of force onto the implant bone structure, which in these cases is right in the process of construction and reconstruction. This system can probably tolerate specific physiological forces, which may even have a stimulating effect; however, if the forces become too great, the tolerance is worn down, leading not to osseointegration, but rather to connective tissue cutting into the implant.

It has been found that physiological stimulation of osseointegration by reduced chewing forces improves the result (G Romanos et al., J. Periodontol. 2003, 74 (10), 1483-1490).

Following these findings, what is known as the progressive bone loading method has been described (R. Appleton et al., Clin. Oral Implants Res. 2005, 16 (2), 161-167). In this method, the forces must be transmitted slowly to the bone. This rising transmission of force is referred to as "progressive loading". In this case, use is first made of a plastics material-based temporary appliance (a temporary supraconstruction) which first ensures that the temporary denture (the temporary appliance) does not occlude with its antagonist. In this time, the patient is advised to eat only liquid or puréed food. Finally, the temporary appliance is modified in such a way that it is brought in a plurality of steps closer and closer to the antagonistic tooth until it is finally in occlusion with the opposing jaw. The jaw bone is intended to adapt during this period of rising loading until eventually the final attendance is carried out.

The resulting bone training is intended to cause slow reconstruction processes, induced by physiological and reduced forces, of the bone architecture. Specifically this bone architecture is important for physiologically distributing forces in the bone, as this is a basic principle of nature and of the bone.

In the prior art, the temporary denture is made from conventional dental prosthesis plastics materials. Radically polymerizable acrylates are preferably used for this purpose. These systems are exhaustively described in the literature, i.e. for example in EP 270915, in EP 630640, in U.S. Pat. No. 6,063,830, in U.S. Pat. No. 5,548,001, in U.S. Pat. No. 4,617,327, and also in EP 0677286.

In addition to the systems based on acrylate chemistry, Spiro orthoesters and polycyclic ketal lactones have been proposed for the production of dental materials (U.S. Pat. No. 4,387,215). DE 19506222 describes cationically polymerizable materials based on oxetane and oxacyclobutane derivatives. Furthermore, bicycloaliphatic 2-methylene-1,3-dioxepanes are known from DE 4439485. U.S. Pat. No. 5,665,839 discloses radically polymerizable oxathiepanes, DE 19612004 describes radically polymerizable multifunctional vinylcyclopropane derivatives, whereas DE 102004002178 proposes monomers which can crosslink by ring-opening metathesis.

An inherent feature of all these systems is the fact that the resulting dental mold material has in principle a thermoset character.

The conventional method with the comparatively long taking times has the drawback that these reconstruction processes do not occur slowly and continuously, as the jaw bone is first not loaded over a relatively long period of time (no occlusion with the opposing jaw) and later experiences a sudden relative full loading by the temporary appliance or the final attendance (supraconstruction), which can also lead to implant losses.

The immediate loading method is disadvantageous, since it has been found in the past to harbor the risk that the reconstructing bone implant boundary will be overloaded; in this early phase of taking, this can then mean the loss of the implant.

A drawback of the progressive bone loading method is the fact that patients may eat only purée and that the fact that no functional chewing forces are then produced leads to no controllable reduced introduction of force compared to a situation in functional full loading. Should however the patient eat food which requires chewing, the chewing forces acting on the implant cannot be controlled.

The primary object of the present invention was to disclose a temporary supraconstruction for a dental implant, with the aid of which the drawbacks associated in each case with the use of conventional temporary supraconstructions can be minimized. In particular, the temporary construction is intended to allow loading of the implant, in particular loading by physiological forces as defined above, which is more readily controllable or lower compared to the situation on use of a conventional temporary supraconstruction.

Surprisingly, it has been found that this object can be achieved by a temporary supraconstruction for a dental implant or a core for a temporary supraconstruction for a dental implant consisting of a material having a modulus of elasticity (E-modulus) of less than 300 MPa.

The term "core" relates in this case to an element which is intended to be provided with a cap or which is already provided with a cap, wherein the combination of the core and cap is a temporary supraconstruction (see below for further details).

A modulus of elasticity of 300 MPa or higher is disadvantageous for attaining an introduction of physiological force. Preferably, the modulus of elasticity should lie in the range of from 15 to 200 MPa, in particular in the range of from 15 to 150 MPa. The modulus of elasticity is in this case measured at 23° C., 50% relative humidity of air and a feed rate of 1 mm/min. The material to be used in accordance with the invention is therefore elastic and relatively pliable (soft, having low rigidity) compared to healthy hard tooth substance (E-moduli: tooth enamel 75 to 90 GPa, dentin 10 to 20 GPa). The elasticity should be preserved for the duration of the application. Preferred materials of this type are also said to be permanently elastic. Preferably, a temporary supraconstruction according to the invention has a particularly high restoring ability, i.e. a capacity to return, after deformation, to its original shape. The dimensional stability in accordance with ISO 4823:2000 should preferably be 99% or higher. As described hereinbefore, the term "temporary supraconstruction" refers to a supraconstruction which is intended from the outset to be replaced by another supraconstruction at a later point in time. Generally, a temporary supraconstruction of this type is provided to remain in the mouth for a few days, weeks or months, until attendance is carried out with a final supraconstruction. The temporary supraconstruction according to the invention can be connected to the dental implant immediately after the implantation (immediate loading) or after a shortened or conventional taking time (for example 3 to 6 months), preferably in such a way that the temporary supraconstruction is in occlusion with the opposing jaw. The temporary supraconstruction can thus ensure that chewing forces are accommodated and, owing to the suppleness and flexion of the temporary supraconstruction, transmitted to the implant in reduced form. Preferably, various temporary supraconstructions of rising hardness ensure during the taking phase that the surface of contact between the implant and jaw bone is subjected to increasing loads. The patients do not have to restrict themselves to purée, but rather can themselves determine their food in accordance with the functional eating and chewing function of their temporary supraconstruction. In addition, the use of a temporary supraconstruction according to the invention is advantageous for aesthetic reasons, as no tooth gap occurs.

Preference is given to a temporary supraconstruction according to the invention or to a core according to the invention for a temporary supraconstruction, wherein the temporary supraconstruction is a temporary crown. The term "crown" refers in the context of the present text to an element which is intended for replacement of an individual tooth and the retention of which on another element is based substantially on a form-fitting connection or force-transmitting connection between (at least a part) of its inner surface and an outer surface of the other element. Preferably, a crown is approximated to the natural geometry of the tooth. This makes a controlled introduction of force particularly readily possible. A temporary supraconstruction according to the invention can however also be a temporary bridge abutment.

In a preferred temporary supraconstruction according to the invention or a preferred core according to the invention, the material to be used has a Shore A hardness in the range of from 20 to 90 or a Shore D hardness in the range of from 30 to 50.

Preferably, in a temporary supraconstruction according to the invention or a preferred core according to the invention, the material to be used can be produced by hardening a hardenable starting material. Preferably, the hardening is a self-hardening. The term "self-hardening" refers in the context of the present text to a hardening which does not require (a) a substantially increased temperature compared to room temperature (for example 65° C. and higher) (a corresponding starting material is also said to be cold-hardening) and (b) irradiation with electromagnetic waves (for example visible light or microwaves).

Preference is given to a temporary supraconstruction according to the invention or to a core according to the invention, wherein the hardenable starting material consists of or comprises the following constituents:
    (a) one or more silicones comprising polyatomic crosslinkable groups, preferably unsaturated crosslinkable groups, and/or one or more optionally substituted, crosslinkable polyethers,
    (b) one or more catalysts or starters for the crosslinking,
    (c) optionally one or more crosslinking agents for which the following applies: the crosslinking agent or agents are not silicones comprising polyatomic crosslinkable groups and not optionally substituted polyethers,
    and
    (d) optionally one or more inorganic or organic fillers.

Polyatomic crosslinkable groups are groups which (i) can enter into a reaction with the aid of which molecules of the one or more silicones of constituent (a) can be covalently linked with one another and/or with other constituents, in particular constituent (c), and which (ii) consist not merely of one atom (for example H). According to the invention, it is possible and in some cases advantageous to use silicones of constituent (a) in which polyatomic crosslinkable groups and Si—H bonds are present in a molecule. In particular in a case of this type, constituent (c) may be dispensed with.

Catalysts of constituent (b) are in particular used if constituent (a) comprises silicones; and starters of constituent (b) are in particular used if constituent (a) comprises polyethers. Catalysts and starters cause a crosslinking of the crosslinkable groups of constituent (a), optionally including crosslinkable groups of a crosslinking agent according to constituent (c). A crosslinking agent according to constituent (c) comprises crosslinkable groups which are provided for reacting with crosslinkable groups of constituent (a).

In principle, all inert materials are suitable as fillers of constituent (d). Preferably, the fillers have an influence on the E modulus and/or the hardness and/or influence the consistency of the starting material. Examples of inorganic fillers are glasses, silicon dioxide (for example as quartzes, cristobalites, pyrogenic $SiO_2$ such as for example that offered under the name AEROSIL® (Degussa) and/or $SiO_2$ produced using a sol/gel method); examples of organic fillers are acrylates. The fillers are incorporated into the matrix during the abreaction of the reactive constituents (a) and also optionally (b) and/or (c) and impart strength to the hardened material.

Preferably, the material of which the temporary supraconstruction according to the invention consists is dyed, in particular to adapt its color to a color of natural teeth. Examples of chromophoric constituents are for example one or more inorganic or organic fillers of constituent (d) (for example tooth-colored acrylate particles and/or ground quartz). However, additional chromophoric constituents can also be provided as optional component (e), for example small organic dyes such as for example diazo dyes.

The use of silicones and polyethers in dentistry is known.

Most frequently, condensation crosslinking hydroxyl group-containing or addition crosslinking vinyl group-containing silicones and also polyether materials are used as dental casting compounds. In the past, the use of silicones has been known for filling and for closing root canals (DE 3915592, U.S. Pat. No. 3,082,520 and DE 19709531). In addition, EP 1307174 describes the use of silicones as an adhesive and temporary tooth filling material, as an adhesive and temporary cement and also as an adhesive.

The use of silicones and polyethers for producing a temporary denture is to date unknown.

Particular preference is given to a temporary supraconstruction according to the invention or to a core according to the invention, wherein the hardenable starting material consists of or comprises the following constituents:

(i) (a) one or more silicones comprising (as preferred crosslinkable groups) alkenyl groups which are optionally substituted,
(b) one or more catalysts for the crosslinking,
(c) one or more organohydrogenpolysiloxanes without polyatomic crosslinkable groups, preferably one or more alkylhydrogenpolysiloxanes (as preferred crosslinking agents for constituent (a)), and
(d) one or more particulate inorganic or organic fillers, preferably selected from the group consisting of silicon dioxide, metal oxides and acrylates, or (ii) (a) alkylpolysiloxane with terminal hydroxyl groups,
(b) one or more catalysts,
(c) one or more silanes with two or more alkoxy substituents, and or
(d) one or more particulate inorganic or organic fillers, preferably selected from the group consisting of silicon dioxide, metal oxides and acrylates, or (iii) (a) one or more polyalkylene glycols in which the terminal OH groups are replaced by aziridine-comprising groups, wherein preferably one or at least one of the plurality of corresponding polyalkylene glycols has a single or only two different repetitive units containing two to four carbon atoms,
(b) one or more starters, and
(d) one or more particulate inorganic or organic fillers, preferably selected from the group consisting of silicon dioxide, metal oxides and acrylates.

Alternative (i) relates to addition crosslinking silicones. As cold-hardening and self-hardening silicones, they are particularly well suited for producing the temporary supraconstructions according to the invention, as they display very low shrinkage during hardening. The hardening is in this case a hardening which is carried out by hydrosilylation, an addition reaction of organohydrogenpolysiloxanes (polysiloxanes containing on the one hand organic groups and on the other hand Si—H bonds) of constituent (c) to silicones comprising (optionally substituted) unsaturated hydrocarbon groups of constituent (a), generally (optionally substituted) alkenyl groups, preferably vinyl or allyl groups.

It is preferable for reasons of elasticity for one or more of the silicones of constituent (a) comprising optionally substituted alkenyl groups to be linear (i.e. unbranched in the siloxane skeletal structure). In a linear silicone of this type, for each molecule, two of the (optionally substituted) alkenyl groups, in particular vinyl or allyl groups, are arranged at the chain ends (terminally). Optionally, additional groups of this type are located, for increasing the degree of crosslinking, in the middle of the chain (i.e. non-terminally), but preferably not in too high a number—for example, for each molecule, one or two or even no such additional groups in the middle of the chain, as they often cause the hardened material to become more rigid and thus more brittle. The use of branched silicones comprising optionally substituted alkenyl groups in constituent (a) is often also advantageous. It is particularly advantageous to use, in addition to linear silicones, VQM silicones (vinyl-terminated quaternary modified silicones). It is preferable if these consist of molecules each containing one silicon atom which is substituted with four siloxanes chains, located at the end of which is a respective vinyl group. Silicones of this type lead to a gain in hardness of the hardened material, without allowance having to be made for a major loss in flexibility or high brittleness and are thus optionally an alternative to fillers of constituent (d), which in some cases increase brittleness.

Preferably, the organohydrogenpolysiloxanes of constituent (c) are alkylhydrogenpolysiloxanes (polysiloxanes containing on the one hand alkyl groups and on the other hand Si—H bonds), wherein the alkyl groups preferably each contain 1 to 4 carbon atoms and are particularly preferably methyl groups. Organohydropolysiloxanes with at least three Si—H bonds per molecule are used as the crosslinking agent. In addition, organohydrogenpolysiloxanes with two Si—H bonds per molecule can also be used as what are known as chain extenders for influencing the hardening behavior and mechanical strength.

Preferably, the organohydrogenpolysiloxanes of constituent (c) contain for each molecule 2 to 3 Si—H bonds. Terminal Si—H bonds are in this case preferred; optionally, they can however also be present additionally or exclusively in the middle of the chain. Organohydrogenpolysiloxanes containing Si—H bonds in the middle of the chain are preferably comparatively short and are then referred to as "modifiers".

Alternative (ii) relates to condensation crosslinking (cold-hardening and self-hardening) silicones. In this case, alkylpolysiloxanes with terminal hydroxyl groups of constituent (a) are crosslinked with one another by silanes with two or more alkoxy substituents of constituent (c) with cleaving-off of an alcohol. Although alkylpolysiloxanes of constituent (a) with hydroxyl groups in the middle of the chain are also possible in accordance with the invention, they are less preferable, as they generally adversely influence the brittleness of the hardened material. The alkyl groups of the alkylpolysiloxanes of constituent (a) preferably each contain 1 to 4 carbon atoms; methyl groups are particularly preferred. The alkoxy substituents of the silanes of constituent (c) preferably each contain 1 to 4 carbon atoms and are particularly preferably ethoxy. In the latter case, ethanol is cleaved off during the crosslinking.

Alternative (iii) relates to (derivatized) polyethers. In order to form the aziridine derivative of a polyalkylene glycol according to constituent (a), the terminal OH groups of a polyether (polyalkylene glycol) are esterified with unsaturated acids and the resulting esters are subsequently reacted with aziridine (ethyleneimine). Reactive aziridine groups are thus produced at the chain ends. Aziridine is a very reactive three-membered heterocyclic ring and can easily be opened. The presence of a starter (constituent (b)) leads to polyaddition and the constituents abreact to form the crosslinked end product.

Most particularly preferred is a temporary supraconstruction or a core according to the invention as defined hereinbefore (preferably in one of the configurations designated hereinbefore as being preferred), wherein the hardenable starting material consists of or comprises the following constituents:

(i) (a) two or more silicones each comprising both (1) crosslinkable groups selected from the group consisting of vinyl and allyl and (2) alkyl groups, wherein the silicones are preferably vinylmethylpolysiloxanes of different composition,
(b) one or more catalysts preferably comprising platinum or palladium,
(c) methylhydrogenpolysiloxane, and
(d) surface-modified or non-surface-modified $SiO_2$ particles having an average particle diameter of less than 200 nm and also optionally further particulate inorganic or organic fillers, or (ii) (a) polydimethylsiloxane with terminal hydroxyl groups,
(b) tin octoate and/or dibutyl tin laurate, (c) one or more silanes with two or more ethoxy substituents, and (d) surface-modified or non-surface-modified $SiO_2$ particles having an average particle diameter of less than 200 nm and also optionally further particulate inorganic or organic fillers, or (iii) (a) one or more polyalkylene glycols in which the terminal OH groups are replaced by aziridine-comprising groups and the two different repetitive units contain two and four carbon atoms respectively, (b) one or more cationic starters, and (d) surface-modified or non-surface-modified $SiO_2$ particles having an average particle diameter of less than 200 nm and also optionally further particulate inorganic or organic fillers.

In the case of the addition crosslinking silicones (alternative (i)), preference is given to silicones of constituent (a) comprising both crosslinkable groups selected from the group consisting of vinyl and allyl and also alkyl groups, preferably alkyl groups containing in each case 1 to 4 carbon atoms, in particular methyl. Most particularly preferred are vinylmethylpolysiloxanes. These contain terminally dimethylvinylsiloxane units and have preferably an average molecular weight in the range of from 2,500 to 350,000 g/mol. Particularly preferred is the use of a plurality of silicones of different composition, in particular vinylmethylpolysiloxanes having for example different viscosities, for example in the range of from approximately 200, 1,000 and 10,000 mPa*s, or which differ in terms of their average molecular weights. Two silicones, the molecular weight distribution of which has in each case only one maximum, differ for example in terms of their average molecular weights if the molecular weight distribution of their mixture has two maxima.

The surface-modified or non-surface-modified $SiO_2$ particles having an average particle diameter of less than 200 nm of constituent (d) are preferably pyrogenic $SiO_2$ such as is offered for example under the name AEROSIL® (Degussa). These particles influence both the hardness of the hardened material and the consistency of the hardenable starting material and are preferably surface-modified. The particulate inorganic or organic fillers which are optionally further contained in constituent (d) preferably contain silicon and comprise for example ground quartz, for example having an average particle diameter of approx. 10 μm. In the case of alternatives (ii) and (iii), that which was stated hereinbefore also applies to constituent (d).

Preferred catalysts (constituent (b)) for the crosslinking of the condensation crosslinking silicones (alternative (ii)) are tin octoate and/or compounds in which a tin atom is bound to two alkyl groups, preferably butyl, such as for example dibutyl tin laurate.

In alternative (iii), preference is given to the linear copolymers, which, as polyalkylene glycols of constituent (a), have relatively long chains, which consist of ethylene oxide and butylene oxide units and in which the terminal OH groups are replaced by aziridine-comprising groups.

The present invention relates also to a temporary supraconstruction consisting of a core as defined hereinbefore (preferably in one of the configurations designated hereinbefore as being preferred) and a cap for the core, wherein the material of the cap has a higher modulus of elasticity than the material of the core. The cap serves preferably to provide a surface having chewing properties improved compared to the surface of the core (in particular increased abrasion resistance). The material, thickness and shape of the cap are selected and adapted to the core in such a way that the capacity of the core to transmit chewing forces to the implant in reduced form is preserved. The composition of the cap is preferably such that it covers only a portion of the outer surface of the core, wherein this portion comprises the chewing surface. The cap consists preferably of ceramic or of a conventional temporary crown material (for example plastics materials or composites based on plastics materials, for example based on methacrylate-containing compounds such as polymethyl methacrylate (PMMA), bisphenol-A-glycidyl methacrylate (bis-GMA), urethane dimethacrylate (UDMA) or triethylene glycol dimethacrylate (TEGDMA); see also the foregoing discussion of conventional dental prosthesis plastics materials or thermosetting dental mold materials). The cap is for example adhesively bonded onto an associated core or arranged thereon so as to form a clamping fit (optionally with form-fitting connection) in order to produce the temporary supraconstruction.

According to a further aspect, the present invention relates to a kit for producing one or more temporary supraconstructions according to the invention as defined hereinbefore or one or more cores as defined hereinbefore (in each case preferably in one of the configurations designated hereinbefore as being preferred), comprising or consisting of constituent (a), constituent (b), constituent (d) and optionally constituent (c) (as defined above as being related), wherein one or more chromophoric constituents are provided for adapting the color of the one or more temporary supraconstructions to in each case a color of natural teeth, or one or more preformed blanks consisting of a hardened (starting) material as defined hereinbefore, wherein the color of the one or more preformed blanks is in each case adapted to a color of natural teeth.

The chromophoric constituents can be of different chemical nature. In a preferred kit according to the invention, constituent (d) consists or comprises of one or more chromophoric fillers as chromophoric constituents. Examples of these include tooth-colored acrylate particles and/or ground quartz. However, additional chromophoric constituents can also be provided, for example small organic dyes such as for example diazo dyes. These can also be used mixed with other constituents, for example as LSR pigment paste (GE Bayer Silicones) mixed with divinylpolysiloxanes of constituent (a).

The color of the temporary supraconstruction according to the invention or of the preformed blank according to the invention can be based on a conventional color scale for dental purposes. An example is that of the color scale produced by VITA Zahnfabrik. Preferred colors are A1, A2, A3, A3.5, B1, B3 and BL.

In a kit according to the invention, which consists of or comprises constituent (a), constituent (b), constituent (d) and optionally constituent (c), these are selected as defined above as being related. This means, for example, that if the constituents are selected in accordance with the above-described alternative (i), not only constituent (a), but rather also constituents (b) and (d) and, in so far as it is present, constituent (c) are selected in accordance with alternative (i) and not in accordance with another alternative.

The term "a preformed blank" refers to a precursor of a temporary supraconstruction or a core, which generally cannot be connected in unaltered form to an implant, but rather is intended to be adapted in terms of its shape to a specific patient situation, for example by removing (for example cutting-off, grinding-off or another material-removing, shaping method) excesses.

Preference is given to a kit according to the invention for producing a plurality of (for example 2, 3 or more) temporary supraconstructions or cores, the materials of which differ with regard to their moduli of elasticity and/or values of Shore A or Shore D hardness. These are often intended to be successively connected to the dental implant in the order of rising moduli of elasticity or values of Shore hardness. Particular preference is given to a kit according to the invention for producing 3 or more temporary supraconstructions or cores, wherein in each case one or more temporary supraconstructions or cores consist of materials having moduli of elasticity in the ranges of from (i) 15 to 40 MPa, (ii) 55 to 70 MPa and (iii) 100 to 120 MPa and/or of materials having a hardness in the ranges of from (i) Shore A hardness 25 to 45, (ii) Shore A hardness 75 to 85 and (iii) Shore D hardness 35 to 45.

A preferred kit according to the invention comprises or consists of constituent (a), constituent (b), constituent (d) and optionally constituent (c), wherein the hardenable starting material or materials for the one or more temporary supraconstructions or cores can in each case be blended from a first and a second component, wherein the first and the second component together comprise or consist of constituent (a), constituent (b), constituent (d) and optionally constituent (c) and are composed and adapted to one another in such a way that as a result of the mixing of the components the starting material results and the hardening thereof is initiated. This can—depending on the nature of the selected constituents—for example take place in that the first component comprises constituents (a) and (c), but not constituent (b) and the second component comprises constituents (a) and (b), but not constituent (c). It is readily possible for a person skilled in the art to select any other desired options. As a further example, the first component could comprise constituents (a) and (b), but not constituent (c) and the second component could comprises constituents (c) and (d), but not constituent (b).

The first and the second component can be metered in different ways. The components can for example be provided in tubes or bottles. In such a case, blending requires visually volumetric metering. Preferably, in a kit according to the invention, in which the hardenable starting material or materials for the one or more temporary supraconstructions can in each case be blended from a first and a second component, the first and the second component can be blended in a ratio by volume of from 10:1 to 1:10, preferably 4:1 to 1:4, particularly preferably 2:1 to 1:2 and in particular 1:1.

If the first and the second component are both present in the form of a paste (paste/paste systems), then the two components can be pressed out, at a preferably identical strand thickness over the stranded lengths (for example identical strands lengths), on a blending block in accordance with a predefined scaling. One of the components can however also be present in liquid form. For this case, it can be added to a base paste via measuring caps or by means of dropping.

Preferably, the metering is carried out with the aid of a static mixing device, for example automatically with the aid of a cartridge system with a static mixing pipe. A preferred kit according to the invention further comprises a static mixing device. The static mixing device preferably comprises the following elements: a static mixing nozzle connected to a double-chamber cartridge or to two tubular bags, an opening supplied by the static mixing nozzle and also means for at the same time pressing out the content of the two chambers or tubular bags, wherein one chamber or one tubular bag contains the first component and the other chamber or the other tubular bag contains the second component.

Preferably, in a kit according to the invention as defined hereinbefore (preferably in one of the configurations designated hereinbefore as being preferred), the first and the second component are adapted to each other in such a way that after the mixing the crosslinking is completed within a period of from 30 s to 10 min.

Alternatively, a kit according to the invention comprises or consists of, as stated hereinbefore, one or more preformed blanks (having the above-specified properties). Preferably, their shape is already approximated to a respective shape of natural teeth, for example the shape of incisors, canines, premolars and/or molars.

Preferably, a kit according to the invention comprises or consists of a plurality of preformed blanks of identical or different color.

Preferably, a kit according to the invention comprises or consists of a plurality of preformed blanks having different moduli of elasticity and/or values of Shore A or Shore D hardness. This also applies to the special case of a kit respectively comprising merely a preformed blank in which a Shore A hardness can be measured and a preformed blank in which a Shore D hardness can be measured.

A preferred kit according to the invention comprises or consists of 3 or more preformed blanks, wherein in each case one or more preformed blanks have moduli of elasticity in the ranges of from (i) 15 to 40 MPa, (ii) 55 to 70 MPa and (iii) 100 to 120 MPa and/or a hardness in the ranges of from (i) Shore A hardness 25 to 45, (ii) Shore A hardness 75 to 85 and (iii) Shore D hardness 35 to 45. These ranges have proven particularly suitable for the controlled introduction of force onto a dental implant. If corresponding temporary supraconstructions are successively connected to the dental implant in the order of rising moduli of elasticity, then a particularly balanced, gradually rising introduction of force (loading) can take place.

The present invention also relates to a kit comprising or consisting of a plurality of (a) temporary supraconstructions as defined hereinbefore, (b) preformed blanks for temporary supraconstructions as defined hereinbefore or (c) combinations of a respective core for a temporary supraconstruction as defined hereinbefore and an associated cap blank. The cap blank of a combination of this type is intended to be adapted in terms of its shape to a specific patient situation, for example by removing (for example cutting-off, grinding-off or another material-removing, shaping method) excesses. Preferably, in a kit of this type, a single, a plurality of or all of the (a) temporary supraconstructions, (b) preformed blanks and (c) combinations are connected to an abutment for a dental implant. With regard to the preferred configurations of the (a) temporary supraconstructions and (b) blanks, the foregoing discussion applies accordingly.

A further aspect of the present invention relates to an abutment for fastening a temporary supraconstruction according to the invention as defined hereinbefore (preferably in one of the configurations designated hereinbefore as being preferred) comprising or consisting of the following elements:

(A) an element for retention of the temporary supraconstruction according to the invention, (B) a platform for supporting the temporary supraconstruction according to the invention in the direction of force along the longitudinal axis of an implant to which the abutment is fastened or is to be fastened toward the jaw bone into which the implant is inserted or is to be inserted, (C) an element which is embodied as a gingivaformer, wherein element (A) and the temporary supraconstruction are adapted to each other in such a way that the temporary supraconstruction is fastened to element (A) in a form-fitting manner in the direction of force along the longitudinal axis of the implant away from the jaw bone into which it is inserted or is to be inserted. Preferably, this is achieved in that element (A) has one or more undercuts with which the temporary supraconstruction can engage. Preferably, during the production of a blank, an element (A) having undercuts or a comparatively shaped structure is surrounded (for example sheathed) with a hardenable starting material according to the invention which is subsequently hardened.

The temporary supraconstruction according to the invention can however also be connected to a dental implant using a conventional temporary dental cement or solely by inherent friction (frictional engagement), optionally using an abutment (in a configuration according to the invention or not according to the invention). The abutment according to the invention preferably consists of plastics material or metal. Element (A) can have any desired shape; optionally, element (A) also has one or more projections (for example in the manner of fingers) which are able to accommodate forces.

Preference is given to an abutment according to the invention, wherein element (A) and the temporary supraconstruction are adapted to each other in such a way that the temporary supraconstruction is fastened to element (A) in a form-fitting manner counter to a rotational force about the longitudinal axis of the implant. This can for example be achieved in that element (A) has an outline which, viewed from the axis corresponding in function to the longitudinal axis of the implant, is shaped not circularly, but rather for example ovally, in an egg-shaped manner, triangularly (for example in the shape of a rectangular triangle), rectangularly (for example in a square shape), in the shape of another polygon or otherwise, in particular with as little rotational symmetry as possible or without rotational symmetry in order to facilitate insertion and retention in the correct orientation.

A further aspect of the present invention relates to a combination of a temporary supraconstruction according to the invention (with or without cap) as defined hereinbefore (preferably in one of the configurations designated hereinbefore as being preferred) and an abutment according to the invention and/or a dental implant.

Furthermore, the present invention relates to a method for producing a temporary supraconstruction according to the invention as defined hereinbefore or a core as defined hereinbefore (in each case preferably in one of the configurations designated hereinbefore as being preferred) including the following steps:

providing a suitable mold,
providing a hardenable starting material as defined hereinbefore,
filling the mold with the hardenable starting material, and afterwards
crosslinking or further crosslinking the hardenable starting material,
removing the crosslinked material from the mold, and afterwards
optionally adapting the shape of the crosslinked material,
or
providing a kit according to the invention comprising one or more preformed blanks,
adapting the shape of a preformed blank (for example by grinding of an oversized blank).

The foregoing discussion concerning preferred configurations of the temporary supraconstruction according to the invention and of the kit according to the invention also applies accordingly to the method according to the invention.

A further aspect of the present invention relates to the use of a (starting) material as defined hereinbefore for producing a temporary supraconstruction for a dental implant or a core for a temporary supraconstruction for a dental implant.

According to a further aspect, the present invention relates also to a method for temporary attendance to a dental implant for therapeutic and/or cosmetic purposes, including the following steps:

(a) providing a temporary supraconstruction according to the invention as defined hereinbefore, or
providing a plurality of temporary supraconstructions as defined hereinbefore and selecting a temporary supraconstruction,
(b) connecting the temporary supraconstruction to the dental implant and afterwards
(c) waiting for a certain period of time and afterwards
(d) releasing the connection between the temporary supraconstruction and the dental implant,
and optionally afterwards the following steps:
(d) selecting a further temporary supraconstruction provided in step (a),
(e) connecting the temporary supraconstruction selected in step (d) to the dental implant and afterwards
(f) waiting for a certain period of time and afterwards
(g) releasing the connection between the temporary supraconstruction and the dental implant,
(h) repeating steps (d) to (g) until all the temporary supraconstructions provided in step (a) have been connected to the implant and the respective connection has been rereleased.

The method according to the invention for temporary attendance to a dental implant for cosmetic purposes is carried out preferably using only a temporary supraconstruction according to the invention as defined hereinbefore.

In a preferred method according to the invention for temporary attendance to a dental implant, a plurality of temporary supraconstructions consisting of or comprising as core material materials having different moduli of elasticity are provided and successively connected to the dental implant in the order of rising moduli of elasticity.

Preferably, in a method according to the invention for temporary attendance to a dental implant, the temporary supraconstruction which is connected to the dental implant is of the type such that the temporary supraconstruction is in occlusion with the antagonistic teeth when the jaw is closed.

Further aspects of the invention will emerge from the subsequent figures, examples and the patent claims.

BRIEF DESCRIPTION OF THE DRAWINGS

FIG. 2 is a schematic view of a temporary supraconstruction (5, 6) consisting of a core (5) and a cap (6) for the core. The material of the cap has a higher modulus of elasticity than the material of the core and has high abrasion resistance. The composition of the cap is such that it covers only a portion of the outer surface (11) of the core, wherein this portion comprises the chewing surface (12).

DETAILED DESCRIPTION

Example 1

Soft, Medium and Hard Formulation

Figure 1:
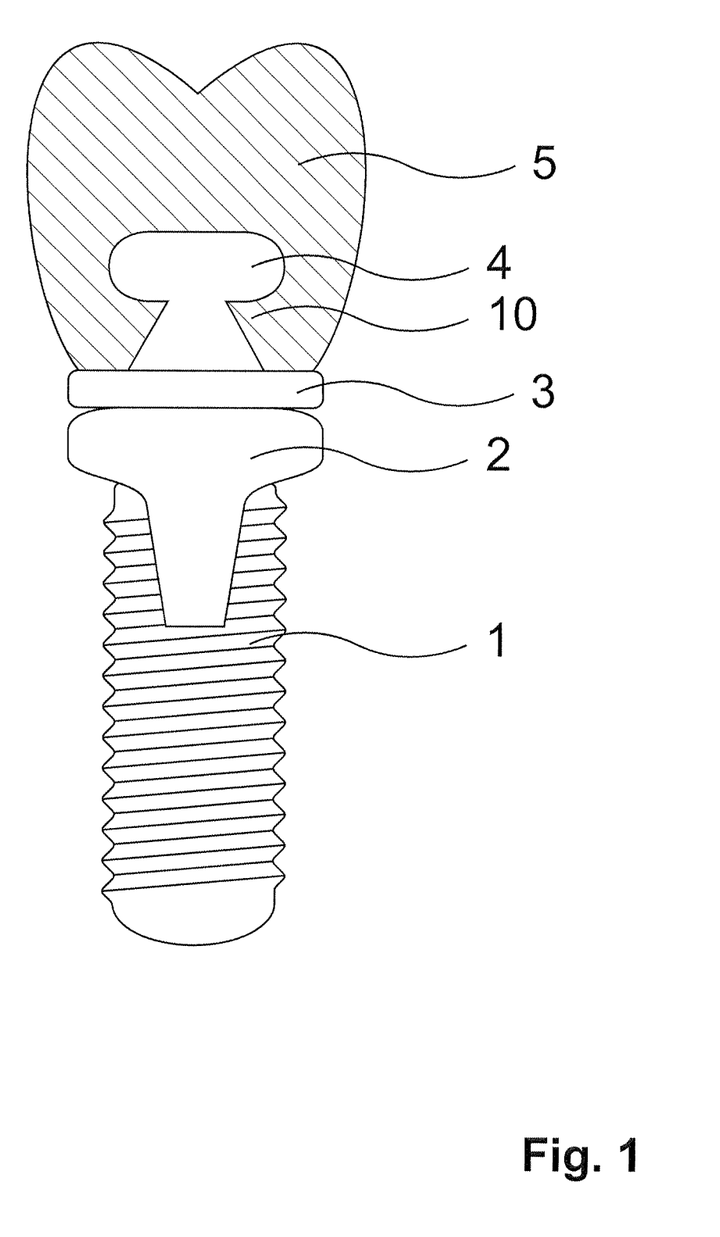
FIG. 1 is a schematic view of a temporary supraconstruction according to the invention (5) in the configuration of a temporary crown which is connected to a dental implant (1) using an abutment (2, 3, 4) according to the invention. An element (A) (4) for retention of the temporary supraconstruction (5) according to the invention has undercuts (10) by means of which the temporary supraconstruction is fastened in a form-fitting manner in the direction of force along the longitudinal axis of the implant (1) away from the jaw bone into which it is to be inserted. Element (C) (2) is embodied as a gingivaformer. A platform (3) is provided as element (B) of the abutment for supporting the temporary supraconstruction (5) in the direction of force along the longitudinal axis of the implant (1) toward the jaw bone into which the implant is to be inserted.
Figure 2:
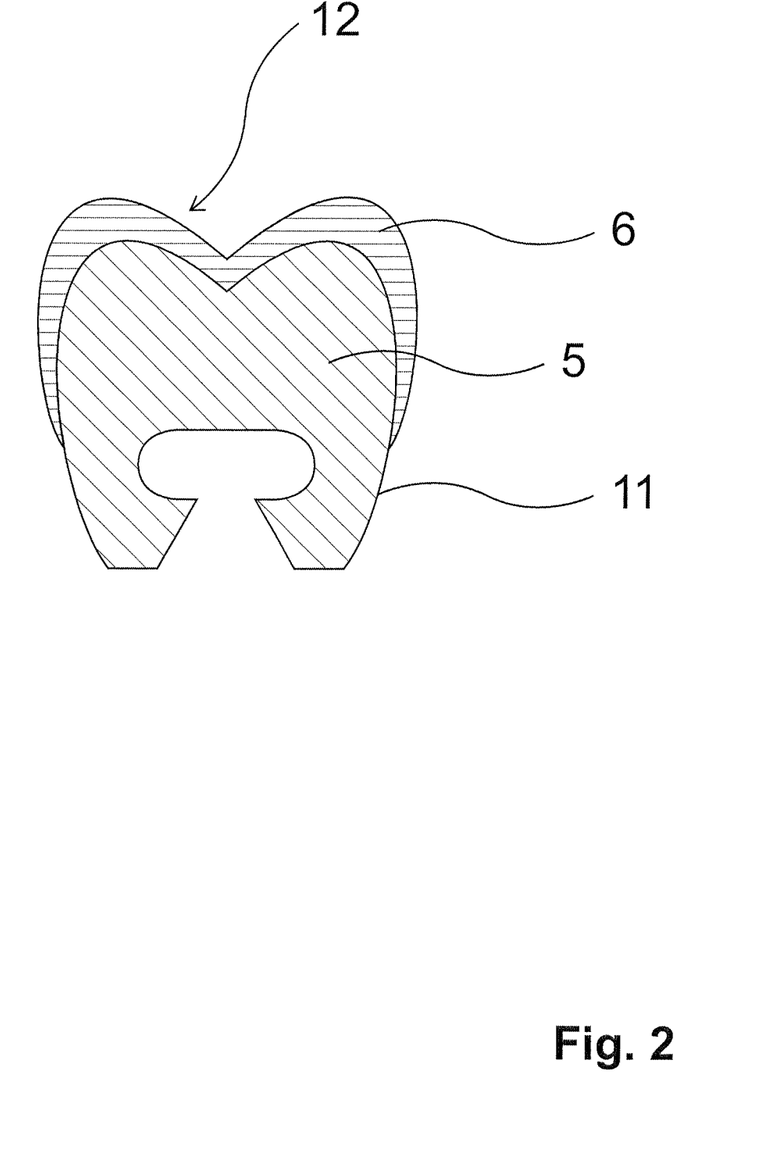

Represented hereinafter are three different hardenable starting materials which can each be produced from a first component and a second component by mixing in a 1:1 ratio by volume and which produce, after hardening, in each case a material which is suitable for a temporary supraconstruction according to the invention. These three materials are characterized as "formulation, soft", "formulation, medium" and "formulation, hard".

1.1 Formulation, Soft

| Reagent | Content [%] | Viscosity [mPa*s] |
|---|---|---|
| First component | | |
| Vinylpolysiloxane | 20.00 | 10,000 |
| Vinylpolysiloxane | 30.00 | 1,000 |
| Vinylpolysiloxane | 8.50 | 200 |
| Methylhydrogenpolysiloxane | 8.10 | 230 |
| Aerosil | 1.00 | |
| Inert filler | 32.40 | |
| Total | 100.00 | |
| Second component | | |
| Polymerization catalyst | 0.50 | 800 |
| Vinylpolysiloxane | 20.00 | 10,000 |
| Vinylpolysiloxane | 35.00 | 1,000 |
| Vinylpolysiloxane | 9.00 | 200 |
| Aerosil | 1.50 | |
| Inert filler | 34.00 | |
| Total | 100.00 | |

1.2 Formulation, Medium

| Reagent | Content [%] | Viscosity [mPa*s] |
|---|---|---|
| First component | | |
| Vinylpolysiloxane | 17.00 | 10,000 |
| Vinylpolysiloxane | 23.00 | 1,000 |
| Vinylpolysiloxane | 7.00 | 200 |
| Methylhydrogenpolysiloxane | 7.00 | 230 |
| Aerosil | 2.00 | |
| Inert filler | 44.00 | |
| Total | 100.00 | |
| Second component | | |
| Polymerization catalyst | 0.50 | 800 |
| Vinylpolysiloxane | 16.50 | 10,000 |
| Vinylpolysiloxane | 28.00 | 1,000 |
| Vinylpolysiloxane | 8.20 | 200 |
| Aerosil | 2.50 | |
| Inert filler | 44.30 | |
| Total | 100.00 | |

1.3 Formulation, Hard

| Reagent | Content [%] | Viscosity [mPa*s] |
|---|---|---|
| First component | | |
| Vinylpolysiloxane | 8.00 | 10,000 |
| Vinylpolysiloxane | 17.00 | 1,000 |
| Vinylpolysiloxane | 6.00 | 200 |
| Methylhydrogenpolysiloxane | 5.00 | 230 |
| Aerosil | 2.00 | |
| Inert filler | 62.00 | |
| Total | 100.00 | |
| Second component | | |
| Polymerization catalyst | 0.50 | 800 |
| Vinylpolysiloxane | 7.00 | 10,000 |
| Vinylpolysiloxane | 21.50 | 1,000 |
| Vinylpolysiloxane | 6.00 | 200 |
| Aerosil | 3.00 | |
| Inert filler | 62.00 | |
| Total | 100.00 | |

The three materials have, in addition to a dimensional stability (restoring ability) of >99% in accordance with ISO 4823:2000, the following properties:

| Formulation | Shore hardness | Modulus of elasticity |
|---|---|---|
| Soft | Shore A approx. 25-45 | approx. 27 MPa |
| Medium | Shore A approx. 75-85 | approx. 63 MPa |
| Hard | Shore D approx. 35-45 | approx. 110 MPa |

Example 2

Manual Blending

An undyed, two-component A silicone (Ufi Gel SC gloss, VOCO) was mixed with tooth-colored acrylic powders (Bosworth Trim®), to produce conventional plastics material temporary appliances, by hand using a spatula on a wax block until consistencies of between completely liquid (little powder) and almost kneadable, but still just free-flowing (little powder), were obtained. With the aid of these materials, it was possible to produce temporary appliances having the various degrees of hardness and accordingly different moduli of elasticity.

Example 3

Cartridge Blending

A low-viscosity A silicone from the cartridge (Contrast light, VOCO) was mixed with further fillers by hand in order to obtain various degrees of hardness, wherein ultimately, in the finished product, the cartridge is also to contain the additional fillers.

Example 4

Tubular Bag Blending

Temporary appliances made of polyether (Impregum®, 3M ESPE) are suitable when they are dyed the color of teeth. They can buffer forces (FIG. 8, 9).

What is claimed:

1. A kit comprising a plurality of (a) temporary supraconstructions, (b) preformed blanks for temporary supraconstructions or (c) combinations of a respective core for a temporary supraconstruction and an associated cap blank, wherein each of said (a) temporary supraconstructions, (b) preformed blanks for temporary supraconstructions or (c) the combinations of the respective cores for said temporary supraconstructions and said associated cap blank comprise an occlusal surface and a material having a modulus of elasticity of less than 300 MPa, and wherein each of (a) said temporary supraconstructions, (b) said preformed blanks for temporary supraconstructions or (c) combinations of said respective cores for the temporary supraconstructions and said associated cap blank comprise materials having different moduli of elasticity values, hardness values, or both, wherein the different moduli of elasticity are from at least two ranges selected from the group consisting of (i) 15 to 40 MPa, (ii) 55 to 70 MPa and (iii) 100 to 120 MPa, and the different hardness values are selected from at least two ranges selected from the group consisting of (i) Shore A hardness 25-45, (ii) Shore A hardness 75-85, and (iii) Shore D hardness 35-45,
wherein the materials are obtained by hardening a starting material,
wherein the starting material comprises the following constituents:
(a) one or more silicones comprising polyatomic crosslinkable groups and/or one or more substituted or unsubstituted crosslinkable polyethers, and
(b) one or more catalysts or starters for causing crosslinking of the crosslinkable groups of constituent (a).

2. The kit as claimed in claim 1, wherein at least one of the (a) temporary supraconstructions, (b) preformed blanks or (c) combinations are adapted for connecting to an abutment for a dental implant by extending over and around said abutment.

3. The kit as claimed in claim 1, wherein the starting material further comprises: (d) one or more inorganic or organic fillers.

4. The kit as claimed in claim 1, wherein the kit comprises at least one (a) temporary supraconstruction.

5. The kit as claimed in claim 1, wherein the kit comprises at least one (b) preformed blank for temporary supraconstructions.

6. The kit as claimed in claim 1, wherein the kit comprises at least one (c) combination of a respective core for a temporary supraconstruction and an associated cap blank.

7. The kit as claimed in claim 1, wherein the starting material comprises the following constituents:
(i) wherein component (a) comprises one or more silicones which comprise substituted or unsubstituted alkenyl groups,
wherein component (b) comprise one or more catalysts for the crosslinking, and wherein said starting material further comprises:
(c) one or more organohydrogenpolysiloxanes without polyatomic crosslinkable groups, and
(d) one or more particulate inorganic or organic fillers;
(ii) wherein component (a) comprises alkylpolysiloxane with terminal hydroxyl groups,
wherein component (b) comprises one or more catalysts, and
wherein said starting material further comprises:
(c) one or more silanes with two or more alkoxy substituents, and
(d) one or more particulate inorganic or organic fillers;
or
(iii) wherein component (a) comprises one or more polyalkylene glycols in which the terminal OH groups are replaced by aziridine-comprising groups, wherein component (b) comprises one or more starters, and
wherein said starting material further comprises (d) one or more particulate inorganic or organic fillers.

8. The kit as claimed in claim 7, wherein the one or more organohydrogenpolysiloxanes without polyatomic crosslinkable groups of constituent (i)(c) comprise one or more alkylhydrogenpolysiloxanes.

9. The kit as claimed in claim 7, wherein the one or more particulate inorganic or organic fillers of (i), (ii) and (iii) are selected from the group consisting of silicon dioxide, metal oxides and acrylates.

10. The kit as claimed in claim 7, wherein one or at least one of the plurality of corresponding polyalkylene glycols of constituent (iii)(a) has a single or only two different repetitive units containing two to four carbon atoms.

11. The kit as claimed in claim 1, wherein the starting material comprises the following constituents:
(i) (a) two or more silicones each comprising both (2) crosslinkable groups selected from the group consisting of vinyl and allyl and (2) alkyl groups,
(b) one or more catalysts comprising platinum or palladium,
(c) methylhydrogenpolysiloxane, and
(d) surface-modified or non-surface-modified $SiO_2$ particles having an average particle diameter of less than 200 nm:
(ii) (a) polydimethylsiloxane with terminal hydroxyl groups,
(b) tin octoate and/or dibutyl tin laurate,
(c) one or more silanes with two or more ethoxy substituents, and
(d) surface-modified or non-surface-modified $SiO_2$ particles having an average particle diameter of less than 200 nm;
or
(iii) (a) one or more polyalkylene glycols in which the terminal OH groups are replaced by aziridine-comprising groups and which have two different repetitive units containing two and four carbon atoms respectively,
(b) one or more cationic starters, and
(d) surface-modified or non-surface-modified $SiO_2$ particles having an average particle diameter of less than 200 nm.

12. The kit as claimed in claim 11, wherein the two or more silicones of constituent (i)(a) are vinylmethylpolysiloxanes having different compositions.

13. The kit as claimed in claim 1, comprising three or more (a) temporary supraconstructions, (b) preformed blanks for temporary supraconstructions or (c) combinations of respective cores for the temporary supraconstructions, wherein the material for each of the three or more components (a), (b) or (c) has a particular modulus of elasticity value and hardness value, wherein the components (a), (b) or (c) have at least three different moduli of elasticity values, hardness values, or both, wherein the modulus of elasticity values are selected from the following ranges: (i) 15 to 40 MPa, (ii) 55 to 70 MPa and (iii) 100 to 120 MPa and/or wherein the hardness value are selected form the following ranges: (i) Shore A hardness 25-45, (ii) Shore A hardness 75-85, and (iii) Shore D hardness 35-45.

14. The kit as claimed in claim 1, comprising three or more temporary supraconstructions.

15. The kit as claimed in claim 1, comprising three or more preformed blanks for temporary supraconstructions.

16. The kit as claimed in claim 1, comprising three or more combinations of respective cores for the temporary supraconstructions and associated cap blanks.

* * * * *